(12) United States Patent
Soetermans (10) Patent No.: US 9,254,077 B2
(45) Date of Patent: Feb. 9, 2016

(54) ENDOSCOPIC APPARATUS HAVING AN OUTER RAIL

(75) Inventor: Maximiliano Soetermans, Pinnacle, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1624 days.

(21) Appl. No.: 12/061,229

(22) Filed: Apr. 2, 2008

(65) Prior Publication Data
US 2008/0249357 A1 Oct. 9, 2008

Related U.S. Application Data

(60) Provisional application No. 60/921,386, filed on Apr. 2, 2007.

(51) Int. Cl.
*A61B 1/018* (2006.01)
*A61B 1/00* (2006.01)
*A61B 1/273* (2006.01)

(52) U.S. Cl.
CPC .............. *A61B 1/018* (2013.01); *A61B 1/0014* (2013.01); *A61B 1/00073* (2013.01); *A61B 1/00105* (2013.01); *A61B 1/2736* (2013.01)

(58) Field of Classification Search
CPC ........... A61B 1/00124; A61B 1/00128; A61B 1/0014; A61B 1/0015; A61B 1/05; A61B 1/0073; A61B 2017/00296
USPC ......... 600/104, 114, 124, 128, 153, 154, 102, 600/113, 115, 123, 156–157; 604/523–525, 604/533, 534
See application file for complete search history.

(56) References Cited

U.S. PATENT DOCUMENTS 5,489,256 A * 2/1996 Adair .............................. 600/133
5,827,190 A * 10/1998 Palcic et al. .................... 600/476

(Continued)

FOREIGN PATENT DOCUMENTS

EP 1 284 120 A1 2/2003
EP 1 477 105 A1 11/2004

(Continued)

OTHER PUBLICATIONS

International Search Report—PCT/US2008/059114 (Sep. 15, 2008).

*Primary Examiner* — Anhtuan T Nguyen
*Assistant Examiner* — Rajaa El Alami
(74) *Attorney, Agent, or Firm* — Brinks Gilson & Lione (57) ABSTRACT

An endoscope apparatus for endoscopic treatment is disclosed. The apparatus comprises an endoscopic insertion tube comprising an outer surface including an outer rail formed longitudinally thereon and extending along a portion of the insertion tube. The outer rail has a predetermined shape. The insertion tube comprises an inner channel formed therethrough. An endoscope apparatus for endoscopic treatment is disclosed. The apparatus comprises an endoscopic insertion tube without a working channel and an outer surface including at least one outer rail formed longitudinally thereon and extending along a portion of the insertion tube. The outer rail has a first predetermined shape. At least one medical device includes an outer wall having at least one mounting unit formed thereon along a portion of the length of the outer wall. The mounting unit has a second predetermined shape cooperable with the first predetermined shape. The second predetermined shape is formed to complement and slidably cooperate with the first predetermined shape of the outer rail for slidably attaching the medical device thereto.

19 Claims, 6 Drawing Sheets

(56) References Cited

U.S. PATENT DOCUMENTS

| | | | |
|---|---|---|---|
| 5,944,654 A * | 8/1999 | Crawford | 600/157 |
| 6,302,917 B1 | 10/2001 | Dua et al. | |
| 6,569,085 B2 * | 5/2003 | Kortenbach et al. | 600/104 |
| 6,878,106 B1 * | 4/2005 | Herrmann | 600/104 |
| 7,029,435 B2 * | 4/2006 | Nakao | 600/153 |
| 7,431,694 B2 * | 10/2008 | Stefanchik et al. | 600/104 |
| 2003/0036679 A1 | 2/2003 | Kortenbach et al. | |
| 2007/0106113 A1 * | 5/2007 | Ravo | 600/113 |

FOREIGN PATENT DOCUMENTS

| | | |
|---|---|---|
| WO | WO 00/48506 | 8/2000 |
| WO | WO 2007/056374 | 5/2007 |

* cited by examiner

ENDOSCOPIC APPARATUS HAVING AN OUTER RAIL

CROSS-REFERENCE TO RELATED APPLICATIONS

This application claims the benefit of U.S. Provisional Application Ser. No. 60/921,386, filed on Apr. 2, 2007, entitled "ENDOSCOPIC APPARATUS HAVING AN OUTER RAIL," the entire contents of which are incorporated herein by reference.

BACKGROUND OF THE INVENTION

The present invention relates to endoscopic apparatus having outer rail guide systems.

Endoscopic devices have been commonly used for various procedures, typically in the abdominal area. Endoscopy is the examination and inspection of the interior of body organs, joints or cavities through an endoscope. Endoscopy allows physicians to peer through the body's passageways. An endoscopic procedure may be used to diagnose various conditions by close examination of internal organ and body structures and may also guide therapy and repair, such as the removal of torn cartilage from the bearing surfaces of a joint. A biopsy, a procedure involving tissue sampling for pathologic testing, may also be performed under endoscopic guidance. For example, endoscopic procedures include the following known procedures: gastroscopy, sigmoidoscopy and colonoscopy, esophago gastro duodenoscopy (EGD), endoscopic retrograde cholangiopancreatography (ERCP), and bronchoscopy.

An endoscope typically includes at least one separate port or working channel. Such port(s) may be used to introduce endoscopic instruments such as catheters, forceps, scissors, brushes, snares or baskets for tissue excision, sampling, or other diagnostic and therapeutic work. The inner diameter of such working channels or ports may vary based on the instruments used during an endoscopic procedure, affecting the overall outer diameter size of the insertion tube of the endoscope. The differences in diameter typically affect the resulting size of the outer diameter of the endoscope. Moreover, as clinicians may use a number of various sized medical devices during an endoscopic procedure, they face challenges in maintaining wire guide position in certain anatomy, e.g., within the biliary tree, while executing an endoscopic procedure.

Thus, it is desirable to provide an improved endoscope apparatus that allows a clinician the ability to use various sizes of medical devices with one endoscope while maintaining longitudinal positioning within a patient's gastrointestinal anatomy.

BRIEF SUMMARY OF THE INVENTION

The present invention generally provides an outer rail endoscopic apparatus including an outer rail guide system that allows a clinician the ability to use various sizes of medical devices with one endoscope while maintaining longitudinal positioning within a patient's gastrointestinal anatomy.

In one embodiment, the present invention provides an endoscope apparatus for endoscopic treatment. The apparatus comprises an endoscopic insertion tube comprising an outer surface including an outer rail formed longitudinally thereon and extending along a portion of the insertion tube. The outer rail has a predetermined shape. The insertion tube comprises an inner channel formed therethrough. An endoscope apparatus for endoscopic treatment is disclosed. The apparatus comprises an endoscopic insertion tube without a working channel and an outer surface including at least one outer rail formed longitudinally thereon and extending along a portion of the insertion tube. The outer rail has a first predetermined shape. At least one medical device includes an outer wall having at least one mounting unit formed thereon along a portion of the length of the outer wall. The mounting unit has a second predetermined shape cooperable with the first predetermined shape. The second predetermined shape is formed to complement and slidably cooperate with the first predetermined shape of the outer rail for slidably attaching the medical device thereto.

In another embodiment, the present invention provides an endoscopic apparatus having an outer rail system for endoscopic treatment. The apparatus comprises the endoscopic apparatus and at least one medical device including an outer wall having at least one mounting unit formed thereon along the length of the outer wall. The mounting unit is configured to slidably mate with the outer rail of the insertion tube for attaching the medical device thereto.

In yet another example, the present invention provides a method of using an endoscopic apparatus having an outer rail system for endoscopic treatment. The method comprises introducing the endoscopic apparatus in the gastrointestinal tract of a patient to an interventional location therein. The method further comprises maintaining position of the apparatus at the interventional location and introducing the medical device through the proximal end of the insertion tube. The method further comprises advancing the medical device beyond the distal end of the insertion tube for enhanced endoscopic treatment.

Further objects, features, and advantages of the present invention will become apparent from consideration of the following description and the appended claims when taken in connection with the accompanying drawings.

DETAILED DESCRIPTION OF THE INVENTION

The present invention generally provides an outer rail endoscopic apparatus that allows a clinician the ability to use various sizes of medical devices with one endoscope while maintaining longitudinal positioning within a patient's gastrointestinal anatomy. This feature also allows for a smaller or relatively reduced diametric size of the insertion tube. The reduced diameter of the insertion tube allows the clinician to be able to more easily perform an endoscopic treatment within a patient's anatomy (e.g., within the biliary duct) that otherwise would not be possible or would be a relatively high risk procedure. Each of the embodiments of the present invention comprises an insertion tube having an outer surface with an outer rail. Each outer rail is configured to cooperate with a mounting unit formed on a medical device (e.g., a wire guide or catheter) to be used during the endoscopic treatment. The medical device is slidably attachable to the side of the insertion tube at its proximal end and is distally advanced beyond the distal end of the insertion tube. This aspect allows enhanced positioning and treatment in areas of the anatomy otherwise unobtainable. Additionally, scope repairs would be reduced as the scope would not have to be sent out for repairs to the accessory channel.

Figure 1A:
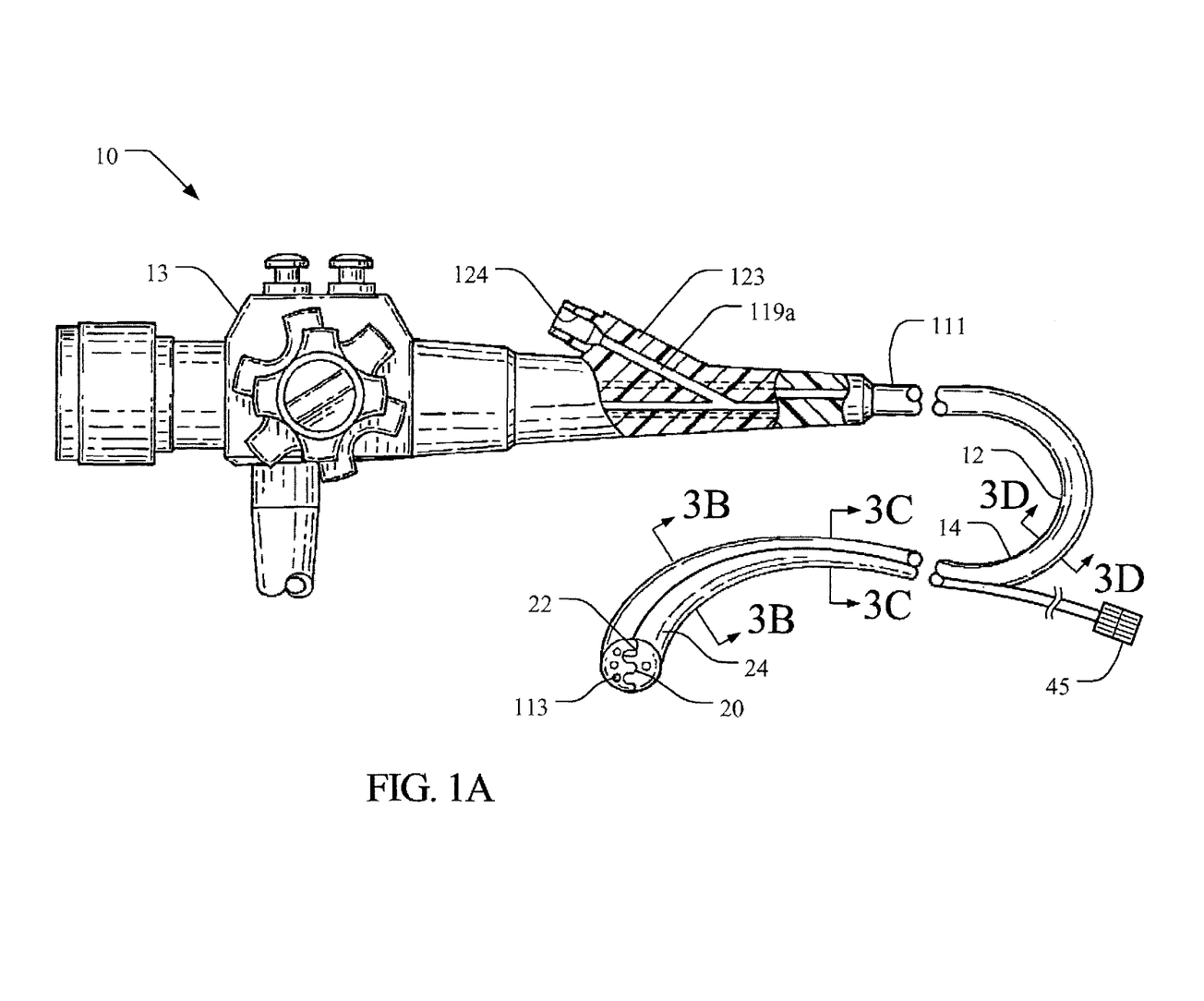
FIG. 1A is an elevated view of an outer rail endoscopic apparatus in accordance with one embodiment of the present invention.
Figure 1B:
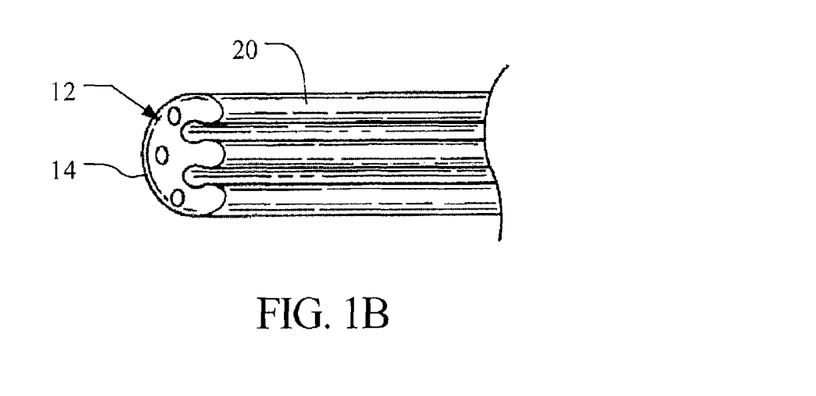
FIG. 1B is a side view of the insertion tube of the apparatus of FIG. 1A.

FIG. 1A illustrates an endoscopic apparatus 10 having an outer rail system for enhanced endoscopic treatment in accordance with one embodiment of the present invention. As shown, the endoscopic apparatus 10 comprises a flexible insertion tube 12 and a control system 13 in communication with the insertion tube 12. As shown in FIGS. 1A and 1B, the flexible insertion tube 12 comprises an outer surface 14 including at least one outer rail 20 formed thereon. Preferably, the outer rail 20 comprises a first predetermined portion or shape 22 (discussed in greater detail below) to accommodate a complementary shape for attaching a medical device 24 thereto. In this embodiment, the outer rail 20 is formed on the outer surface 14 along the length of the insertion tube 12.

The outer rail 20 is formed on the outer surface 14 of the insertion tube 12 and replaces a conventional endoscopic working channel typically formed through the insertion tube 12 of an endoscope, thereby defining a smaller or reduced diametric size of the insertion tube 12. The outer rail 20 is configured to allow a medical device 24, e.g., a wire guide, to be slidably interlocked therewith and advanced relative to the insertion tube 12. The first predetermined shape 22 of the outer rail 20 may take on any suitable shape that allows a complementary or cooperating shape to be able to slide through and lock itself thereon. For example, as shown in FIGS. 2-5, the outer rail 20 of the insertion tube 12 is an interlocking rack that is configured to interlock with a complementing or cooperating shape formed along the length of a medical device 24, e.g., a wire guide or catheter. The medical device 24 may be distally advanced beyond the distal end of the insertion tube 12 to reach areas of an anatomy otherwise unobtainable by a conventional endoscope.

As mentioned above, the outer rail 20 replaces a conventional endoscopic working channel typically formed through the insertion tube 12. As shown, the insertion tube 12 does not have a conventional endoscopic working channel. Rather, the insertion tube 12 comprises at least one inner channel in which endoscopic components are disposed, defining a reduced outer diameter occupied by the insertion tube 12. In this embodiment, the endoscopic components vary depending on the purpose of use for the endoscope. For example, the apparatus 10 includes any number of inner channels. In this embodiment, there are three inner channels shown in FIGS. 1A-5. As shown, an illumination channel 32 is formed through the insertion tube 12 through which a fiberoptic cable is inserted for the transmission of light from a light source. Moreover, a viewing channel 34 can also be provided with a fiberoptic cable for viewing purposes and a fluid channel 36 can be provided for application of suction at the surgical site. In another example, the inner channel may be a fluid channel, a light channel, and a camera channel formed through the insertion tube to allow for fluid, light, and a camera, respectively therethrough.

The endoscopic apparatus 10 shown in FIG. 1A further comprises a control system 13 in mechanical and fluid communication with the insertion tube 12. The control system 13 is configured to control at least one of the endoscopic components. It is to be understood that any other suitable endoscopic operating control system 13 may be used with the insertion tube 12 described above without falling beyond the scope or spirit of the present invention. In one embodiment, the control system 13 includes an auxiliary port portion 123 having a proximal opening 124. The fluid channel 36 extends into the auxiliary port 123 by way of a fluid channel extension 119a. Each of the channels preferably opens at the distal or insertion end 113 of the flexible section 12 of the endoscopic apparatus 10.

The control system 13 of the endoscopic apparatus 10 shown in FIG. 1A can be of many different types so long as it is in fluid and mechanical communication with the inner channels formed through the insertion tube 12 of the endoscopic apparatus 10. While most of the working components of these control systems 13 are similar, each may have a different configuration without falling beyond the scope or spirit of the present invention. For example, the proximal opening and the auxiliary port may differ amongst each other. Each of these specifically identified control systems, and other commercially available endoscopes, utilize different sealing members (not shown) at the proximal opening of the auxiliary port. It is understood that the various aspects of the present invention accommodate the secure attachment to various configurations and dimensions of a variety of endoscopes.

As shown, the endoscopic apparatus 10 further comprises at least one medical device 24 having an outer wall 42 comprising at least one mounting unit 44 formed thereon along the length of the outer wall 42. In this embodiment, the mounting unit 44 is configured to slidably mate with the outer rail 20 of the insertion tube 12 for slidably attaching the medical device 24 thereto. Preferably, the mounting unit 44 has a second predetermined portion or shape 46 cooperable with the first predetermined shape 22. The second predetermined shape 46 is formed to complement and slidably cooperate with the first predetermined shape 22 of the outer rail 20 for slidably attaching the medical device thereto.

In this example, this is accomplished by having the second predetermined shape 46 take on a complementing shape relative to the first predetermined shape 22. As shown in FIGS. 2-5, the medical device 24 slidably interlocks with the insertion tube 12 due to the cooperating relationship between the outer rail 20 and the mounting unit 44.

In this example, the outer rail 20 is configured to proximally taper or distally flare longitudinally along the outer surface 14 of the insertion tube 12 to receive the mounting unit 44. As shown in FIGS. 1A, 2, and 3A-D, the mounting unit 44 is slidably received by the outer rail 20 at a proximal portion of the insertion tube 12. The mounting unit 44 extends distally along the insertion tube 12. Although not necessarily, the mounting unit 44 may extend to the distal end of the insertion tube 12 or may end proximal thereto (see FIGS. 1B-D). Moreover, in this embodiment, the mounting unit 44 extends proximally to a hub 45 through which other devices may be introduced through the endoscope.

Figure 1C:
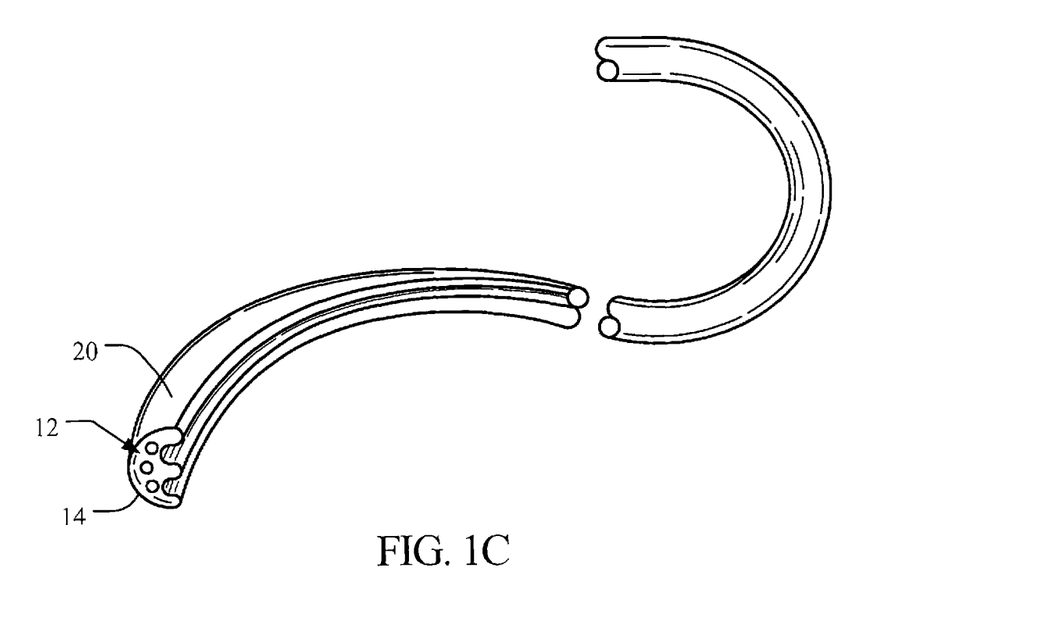
FIG. 1C is a partial view of the insertion tube of the endoscopic apparatus of FIG. 1A.
Figure 1D:
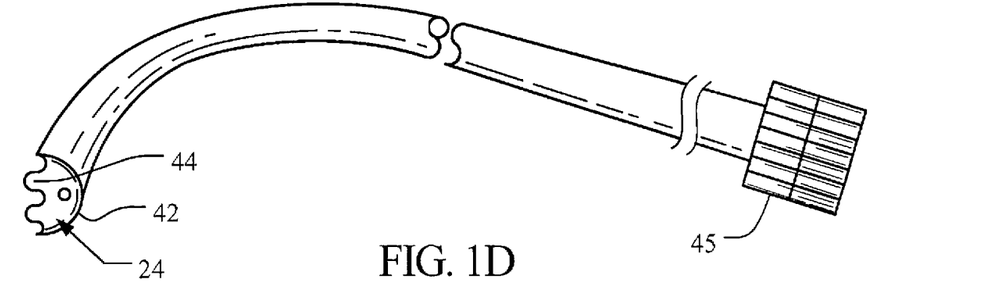
FIG. 1D is a perspective view of a medical device that cooperates with the insertion tube of the endoscopic apparatus of FIG. 1A.
Figure 2:
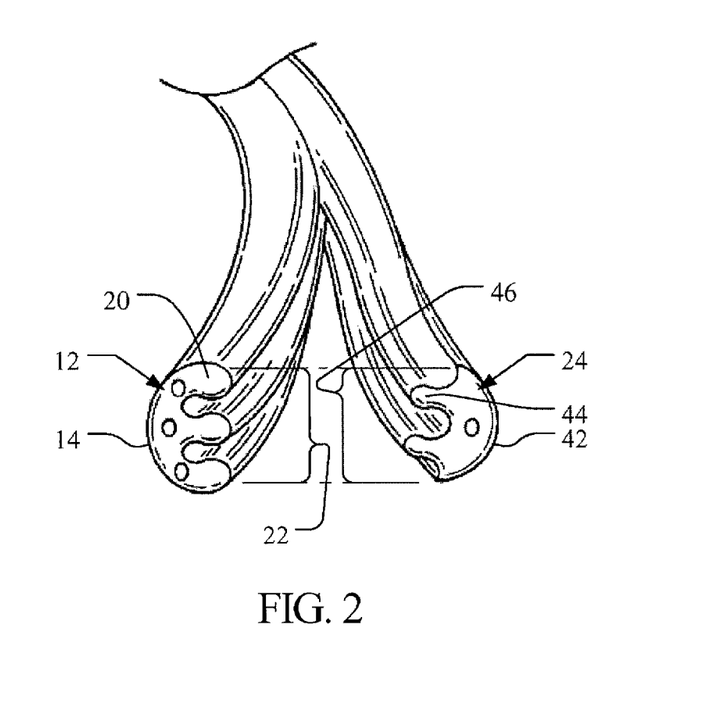
FIG. 2 is a partial exploded view of the apparatus of FIG. 1A.
Figure 3A:
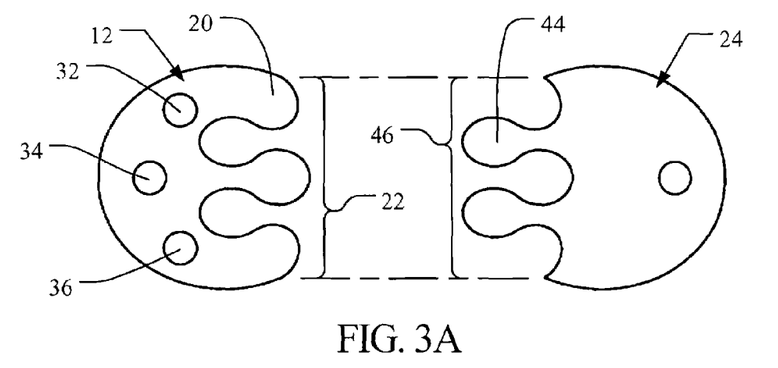
FIG. 3A is an end view of the apparatus of FIG. 1A.
Figure 3B:
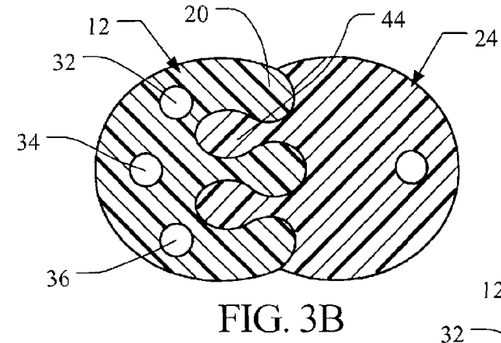
FIG. 3B is a cross-sectional view of the apparatus of 1A taken along line 3B-3B.
Figure 3C:
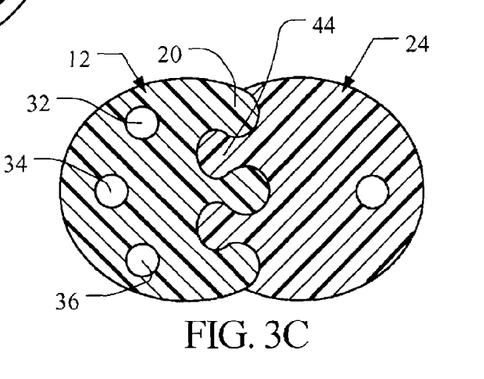
FIG. 3C is a cross-sectional view of the apparatus of 1A taken along line 3C-3C.
Figure 3D:
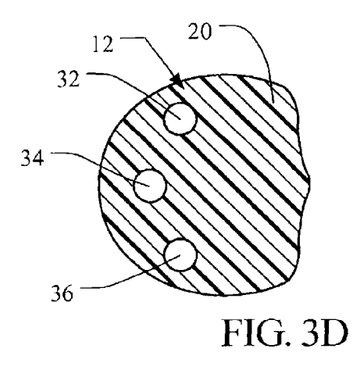
FIG. 3D is a cross-sectional view of the apparatus of 1A taken along line 3D-3D.
Figure 4:
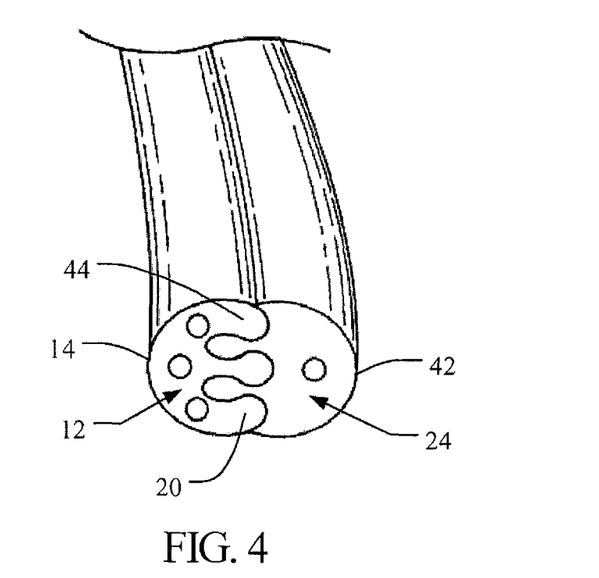
FIG. 4 is a partial view of the apparatus of FIG. 1A.
Figure 5:
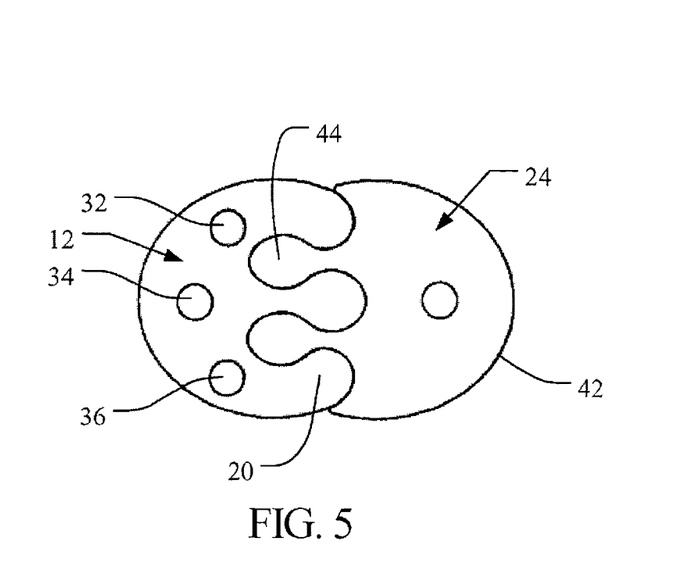
FIG. 5 is an end view of the apparatus of FIG. 4.

As shown in FIG. 1C, in one example, each of the outer rails 20 is formed longitudinally along the outer surface 14 of the insertion tube 12. Preferably, each of the outer rails 20 extends distally on the outer surface 14 to the distal end 113 of the insertion tube 12. In this embodiment, the outer rail 20 is formed with increased prominence distally along the outer surface, having an increased area or depth between each adjacent outer rail 20 at the distal end 113. This allows the mounting unit 44 (see FIG. 1D) to slidably cooperate with the outer surface 14 and attach the medical device 24 to the insertion tube 12.

It is to be understood that each of the outer rails 20 and mounting units 44 may take on any suitable shape. This is possible so long as each outer rail 20 and its corresponding mounting unit 44 are configured to complement each other such that when engaged with each other in a slidably cooperating relationship, the two units are slidably interlocked with each other. Furthermore, depending on the number of outer rails 20 formed on the insertion tube 12, the same number of medical devices 40 may be used with the insertion tube 12 during an endoscopic procedure.

In this embodiment, the insertion tube 12 comprises a proximal end 111 and a distal end 113. Preferably, each outer rail 20 is formed on the insertion tube 12 from the proximal end 111 to the distal end 113 so that the medical device 24 may be slidably introduced at the proximal end 111 and advanced beyond the distal end 113. This may be accomplished by any suitable manner, e.g., by having a tapered formation of the first predetermined shape 22 near the proximal end of the insertion tube 12. The medical device may then be introduced and advanced at the tapered formation to slidably engage the insertion tube 12. In use, e.g., a catheter, may be advanced to a location beyond the distal end of the insertion tube 12 to a stricture within the anatomy otherwise unobtainable with the outer diameter size of a conventional endoscope.

Figure 6:
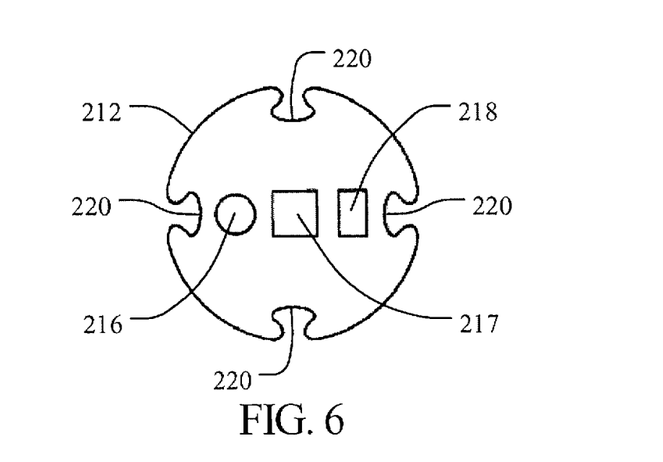
FIG. 6 is an end view of the apparatus in accordance with another embodiment of the present invention.

It is to be noted that the outer rail formed on the insertion tube may simply be one outer rail or a plurality thereof. In the embodiment shown in FIGS. 1a-5, the insertion tube comprises one outer rail formed along the length of the insertion tube. However, the embodiment provided in FIG. 6 includes four outer rails 220. As shown, the insertion tube 212 comprises four outer rails 220 having first predetermined shapes radially formed about the outer surface of the insertion tube. In this embodiment, each of the outer rails 220 has a first predetermined shape that is the same as the others. As shown, the apparatus comprises an illumination channel 216 through which a fiberoptic cable is inserted for the transmission of light from a light source. Moreover, the apparatus comprises a viewing channel 217 having a fiberoptic cable for viewing purposes and a third channel 218 for application of fluid or suction at the surgical site. A corresponding mounting unit having a second predetermined shape of a medical device (not shown) may be used to slidably attach to the outer rail in the similar manner as described above. Thus, a series of accessory channels would be able to engage the outer rail. This would allow the user flexibility during the procedure because the channel could be interchanged or swapped as desired.

Figure 7:
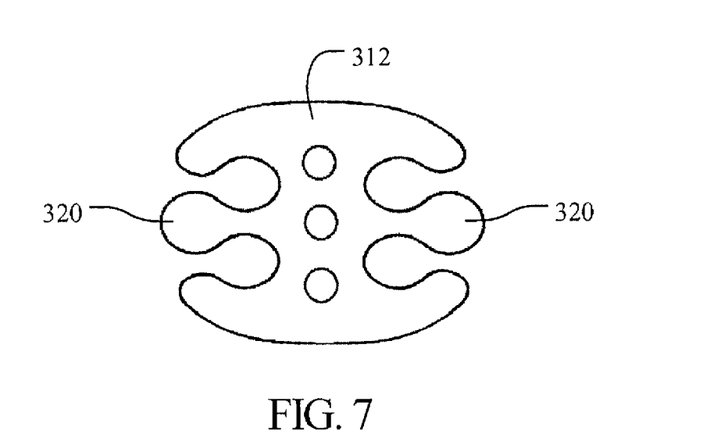
FIG. 7 is an end view of an apparatus in accordance with yet another embodiment of the present invention.

The embodiment provided in FIG. 7 includes two outer rails 320 formed on the insertion tube 312, each of which having a first predetermined shape that is the same as the other. A corresponding mounting unit has a second predetermined shape that may be used to slidably attach to the outer rail in the similar manner as described above. Thus, a series of accessory channels would be able to engage the outer rail. This would allow the user flexibility during the procedure because the channel could be interchanged or swapped as desired. In this embodiment, the apparatus also includes inner channels similar to the inner channels mentioned above.

Figure 8:
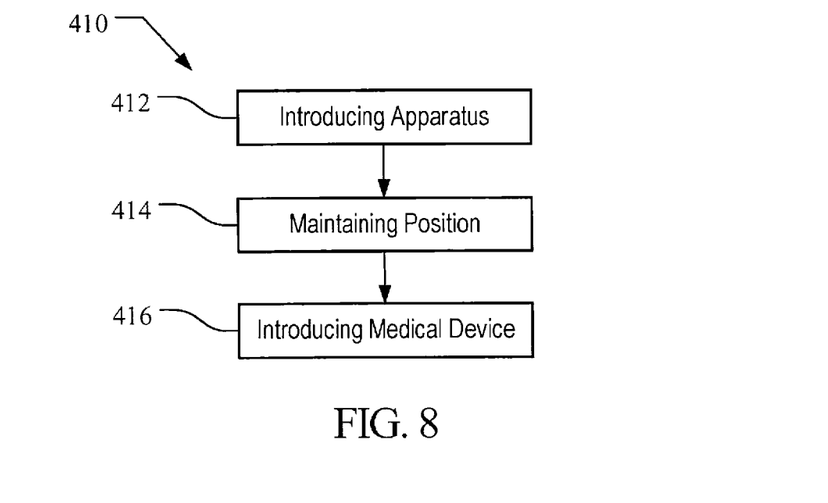
FIG. 8 is a flow chart of one method of using the endoscopic apparatus of FIG. 1 in accordance with one example of the present invention.

FIG. 8 illustrates a flow chart of one method 410 of using the endoscopic apparatus discussed above having an outer rail system for endoscopic treatment. As shown, the method comprises introducing the endoscopic apparatus in the gastrointestinal tract of a patient to an interventional location therein in box 412 and maintaining position of the apparatus at the interventional location in box 414. The method 410 further includes introducing a medical device through the proximal end of the insertion tube. The mounting unit is configured to slidably mate with the outer rail of the insertion tube for attaching a medical device thereto. In this example, this may be accomplished by having the outer rail formed on the outer surface at a proximal portion of the insertion tube. The outer rail may be formed to proximally taper or distally flare to receive the mounting unit which may be slidably attached therewith. The mounting unit may extend proximally from the insertion tube to a port through which a medical device may be disposed for introduction thereof into the patient.

The method 410 further comprises advancing the medical device beyond the distal end of the insertion tube for enhanced endoscopic treatment that allows a clinician the ability to use various sizes of medical devices with one endoscope while maintaining longitudinal positioning within a patient's gastrointestinal anatomy in box 416.

The medical device is preferably provided separately from the endoscopic apparatus with the outer rail(s) already formed along the outer surface of the insertion tube. At a desired time during the use of the flexible insertion tube, the medical device can be slidably engaged along the length of the outer surface of the insertion tube. The medical device may be introduced at the proximal end thereof and then may be slidably advanced beyond the distal end of the insertion tube to a desired location within the anatomy of a patient. Additionally, scope repairs would be reduced as the scope would not have to be sent out for repairs to the accessory channel.

While the present invention has been described in terms of preferred embodiments, it will be understood, of course, that the invention is not limited thereto since modifications may be made to those skilled in the art, particularly in light of the foregoing teachings.

The invention claimed is:

1. An endoscope apparatus for endoscopic treatment, the apparatus comprising:
   an endoscopic insertion tube having a proximal end and extending to a distal end, the endoscopic insertion tube having at least one illumination channel and at least one viewing channel and not having a working channel capable of introducing an endoscopic instrument therethrough, and comprising an outer surface formed into at least one outer rail having an outer rail length, the outer rail formed longitudinally and extending from a proximal portion of the insertion tube to the distal end of the insertion tube, the outer rail having a first predetermined shape;
   at least one medical device including an outer wall having at least one mounting unit formed thereon along a portion of a length of the outer wall, the mounting unit having a second predetermined shape cooperable with the first predetermined shape; the second predetermined shape formed to complement and slidably cooperate with the first predetermined shape of the outer rail for slidably attaching the medical device thereto; and wherein each outer rail is formed with increased prominence along the outer rail length from the proximal portion to the distal end, a diameter of the at least one outer rail comprising the outer surface of the endoscopic insertion tube proximally and gradually decreasing longitudinally to receive the mounting unit.

2. The apparatus of claim 1 wherein the at least one outer rail comprises first and second outer rails formed on the outer surface.

3. The apparatus of claim 2 wherein the at least one medical device comprises first and second medical devices, each having mounting units formed thereon and configured to mate with one of the first and second outer rails.

4. The apparatus of claim 1 wherein the insertion tube comprises a proximal end and a distal end, the at least one outer rail being formed on the insertion tube from the proximal end to the distal end so that the medical device may be slidably introduced at the proximal end and advanced beyond the distal end.

5. The apparatus of claim 1 wherein the first predetermined shape has two grooves, the second predetermined shape being cooperable with the two grooves of the first predetermined shape.

6. The apparatus of claim 1 wherein the at least one mounting unit proximally tapers longitudinally along the outer wall of the at least one medical device to engage the outer rail.

7. The apparatus of claim 3 wherein the at least one mounting unit proximally tapers longitudinally along the outer wall of the at least one medical device to engage the outer rail.

8. The apparatus of claim 4 wherein the at least one mounting unit proximally tapers longitudinally along the outer wall of the at least one medical device to engage the outer rail.

9. An endoscope apparatus for endoscopic treatment, the apparatus comprising:

an endoscopic insertion tube having at least one illumination channel and at least one viewing channel and not having a working channel capable of introducing an endoscopic instrument therethrough, and comprising an outer surface formed into at least one outer rail, the outer rail formed longitudinally thereon and extending along a portion of the insertion tube, the outer rail having a first predetermined shape;

at least one medical device having a proximal end and extending to a distal end, the medical device having including an outer wall having at least one mounting unit having a mounting unit length formed thereon and extending from a proximal portion of the outer wall to the distal end of the medical device, the mounting unit having a second predetermined shape cooperable with the first predetermined shape; the second predetermined shape formed to complement and slidably cooperate with the first predetermined shape of the outer rail for slidably attaching the medical device thereto; and wherein each mounting unit is formed with increased prominence from the proximal portion to the distal end, a diameter of the at least one mounting unit proximally and gradually decreasing longitudinally along the outer wall of the at least one medical device to engage the outer rail.

10. The apparatus of claim 9 wherein the at least one outer rail comprises first and second outer rails formed on the outer surface.

11. The apparatus of claim 10 wherein the at least one medical device comprises first and second medical devices, each having mounting units formed thereon and configured to mate with one of the first and second outer rails.

12. The apparatus of claim 9 wherein the insertion tube comprises a proximal end and a distal end, the at least one outer rail being formed on the insertion tube from the proximal end to the distal end so that the medical device may be slidably introduced at the proximal end and advanced beyond the distal end.

13. The apparatus of claim 9 wherein the first predetermined shape has two grooves, the second predetermined shape being cooperable with the two grooves of the first predetermined shape.

14. The apparatus of claim 9 wherein the at least one outer rail proximally tapers longitudinally along the outer surface of the insertion tube to receive the mounting unit.

15. The apparatus of claim 11 wherein the at least one outer rail proximally tapers longitudinally along the outer surface of the insertion tube to receive the mounting unit.

16. The apparatus of claim 12 wherein the at least one outer rail proximally tapers longitudinally along the outer surface of the insertion tube to receive the mounting unit.

17. An endoscope apparatus for endoscopic treatment, the apparatus comprising:

an endoscopic insertion tube having at least one illumination channel and at least one viewing channel and not having a working channel capable of introducing an endoscopic instrument therethrough, and comprising an outer surface formed into a plurality of outer rails, the plurality of outer rails formed longitudinally and extending along a portion of the insertion tube, the plurality of outer rails having a first predetermined shape;

at least one medical device including an outer wall having at least one mounting unit formed thereon along a portion of a length of the outer wall, the mounting unit having a second predetermined shape cooperable with the first predetermined shape; the second predetermined shape formed to complement and slidably cooperate with the first predetermined shape of the outer rail for slidably attaching the medical device thereto; and wherein the first predetermined shape has at least two grooves, each groove being located between two adjacent outer rails, the second predetermined shape being cooperable with the at least two grooves of the first predetermined shape, each outer rail being formed with increased prominence distally, a diameter of the at least one outer rail comprising the outer surface of the endoscopic insertion tube proximally and gradually decreasing longitudinally to receive the mounting unit, the mounting unit having at least one element which makes direct contact with two adjacent outer rails when the endoscopic insertion tube and the medical device are in slidable connection.

18. The apparatus of claim 17 wherein the plurality of outer rails comprises first and second outer rails formed on the outer surface.

19. The apparatus of claim 17 wherein the insertion tube comprises a proximal end and a distal end, the at least one outer rail being formed on the insertion tube from the proximal end to the distal end so that the medical device may be slidably introduced at the proximal end and advanced beyond the distal end.

* * * * *